(12) United States Patent
Tily

(10) Patent No.: US 12,402,808 B2
(45) Date of Patent: Sep. 2, 2025

(54) TECHNIQUES FOR APPLICATION PERSONALIZATION

(71) Applicant: Oura Health Oy, Oulu (FI)

(72) Inventor: Harry Tily, London (GB)

(73) Assignee: Oura Health Oy, Oulu (FI)

( * ) Notice: Subject to any disclaimer, the term of this patent is extended or adjusted under 35 U.S.C. 154(b) by 515 days.

(21) Appl. No.: 17/880,474

(22) Filed: Aug. 3, 2022

(65) Prior Publication Data

US 2023/0115575 A1  Apr. 13, 2023

Related U.S. Application Data

(60) Provisional application No. 63/255,285, filed on Oct. 13, 2021.

(51) Int. Cl.
| | |
|---|---|
| *G06F 3/048* | (2013.01) |
| *A61B 5/00* | (2006.01) |
| *A61B 5/0205* | (2006.01) |
| *A61B 5/11* | (2006.01) |

(52) U.S. Cl.
CPC ........ *A61B 5/1118* (2013.01); *A61B 5/02055* (2013.01); *A61B 5/6801* (2013.01)

(58) Field of Classification Search
CPC .. A61B 5/1118; A61B 5/02055; A61B 5/6801
See application file for complete search history.

(56) References Cited

U.S. PATENT DOCUMENTS

| | | | | |
|---|---|---|---|---|
| 11,456,080 | B1* | 9/2022 | Jain | A61B 5/4815 |
| 11,527,316 | B2* | 12/2022 | Crowley | A61B 5/681 |
| 2019/0387998 | A1* | 12/2019 | Garten | A61M 21/00 |
| 2020/0357522 | A1* | 11/2020 | Pahwa | G16H 80/00 |
| 2021/0225482 | A1* | 7/2021 | Crowley | G06F 3/0484 |
| 2021/0342128 | A1* | 11/2021 | Carraway | G06F 9/451 |
| 2023/0115575 | A1* | 4/2023 | Tily | A61B 5/6801 |
| | | | | 600/301 |
| 2023/0215557 | A1* | 7/2023 | Still | G16H 50/20 |
| | | | | 705/2 |
| 2024/0251223 | A1* | 7/2024 | Saarinen | H04W 4/06 |
| 2025/0118041 | A1* | 4/2025 | Gueye | G06T 19/20 |

* cited by examiner

*Primary Examiner* — David Phantana-angkool
(74) *Attorney, Agent, or Firm* — Holland & Hart LLP

(57) ABSTRACT

Methods, systems, and devices for application personalization are described. The method may include receiving physiological data from a wearable device associated with a user and receiving data associated with previous user engagement by the user with user interface features of an application associated with the wearable device. The method may include determining a content layout of the user interface features within the application based on an output of a predictive model. The predictive model may use at least the received physiological data as input and be configured to increase future user engagement with the user interface features based on the received data associated with previous user engagement. In some cases, the method may include causing a graphical user interface of the user device to display the determined content layout of the user interface features.

20 Claims, 10 Drawing Sheets

TECHNIQUES FOR APPLICATION PERSONALIZATION

CROSS REFERENCE

The present application for Patent claims the benefit of U.S. Provisional Patent Application No. 63/255,285 by TILY, entitled "TECHNIQUES FOR APPLICATION PERSONALIZATION," filed Oct. 13, 2021, assigned to the assignee thereof, and expressly incorporated by reference herein.

FIELD OF TECHNOLOGY

The following relates to wearable devices and data processing, including techniques for application personalization.

BACKGROUND

Some wearable devices may be configured to collect physiological data from users, including temperature data, heart rate data, and the like. Many users have a desire for more insight regarding their physical health.

DETAILED DESCRIPTION

Figure 1:
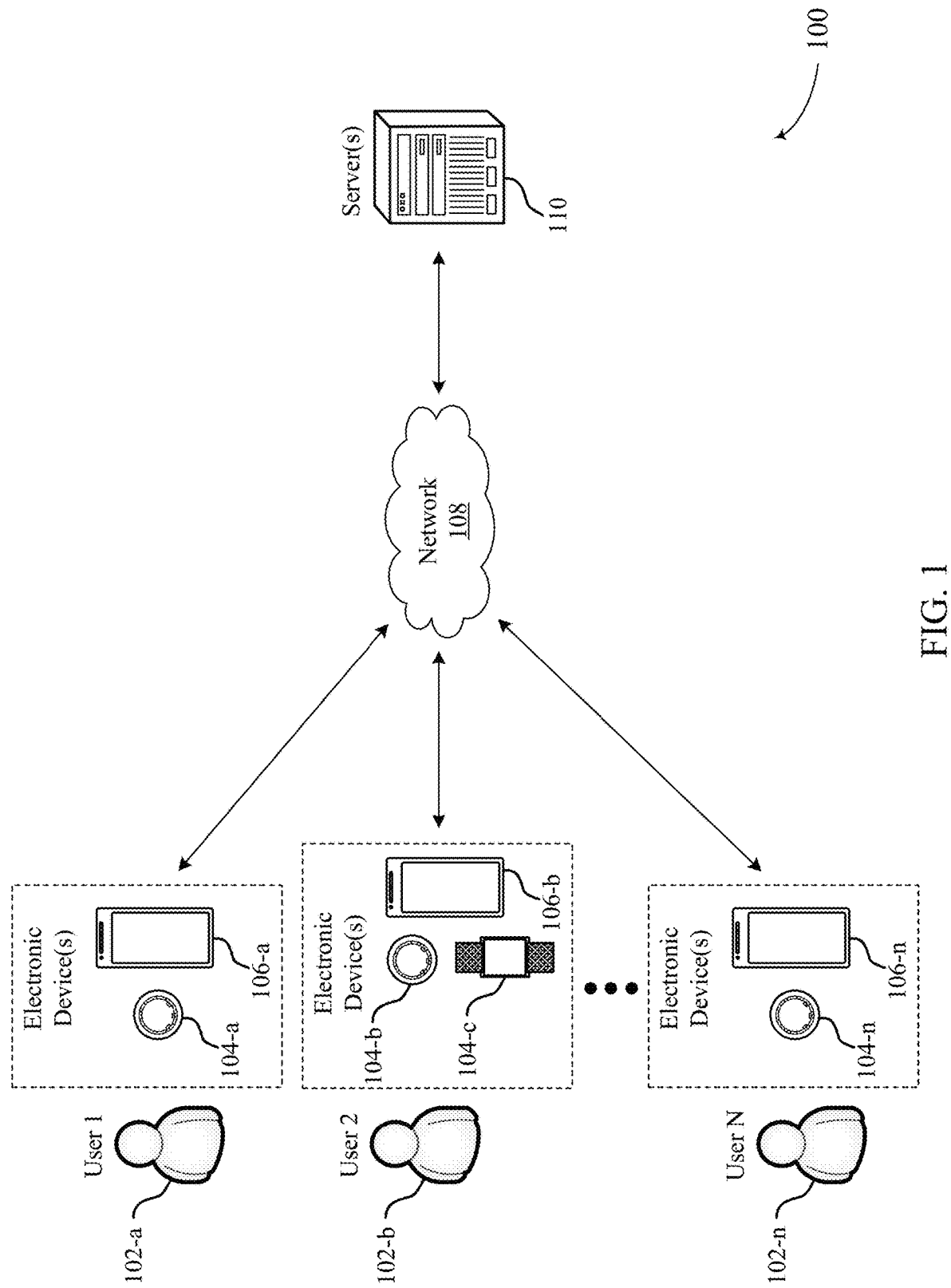
FIG. 1 illustrates an example of a system that supports techniques for application personalization in accordance with aspects of the present disclosure.

Some wearable devices may be configured to collect physiological data from users, including temperature data, heart rate data, and the like. Acquired physiological data may be used to analyze the user's movement and other activities, such as sleeping patterns. Many users have a desire for more insight regarding their physical health, including their sleeping patterns, activity, and overall physical well-being. A wearable device may send measured data and otherwise communicate with a user device running an application or other software associated with the wearable device. The application may display the measured physiological data, patterns, insights, messaging, media content and the like to the user via a user interface in the application. However, the user interface, such as the layout and the subset of content displayed to the user, may be relatively consistent across users, even if different users have wide variations in their health goals and the content or insights that are relevant to them. As such, conventional health monitoring applications associated with wearable devices may be unable to personalize the insights and data displayed for a particular user. As such, conventional techniques for improved application customization are desired.

Aspects of the present disclosure are directed to techniques for application personalization. In particular, computing devices of the present disclosure may receive physiological data from a wearable device associated with a user. In some cases, the computing devices of the present disclosure may receive data associated with previous user engagement by the user with user interface features of an application associated with the wearable device. The user interface features of the application may be an example of home cards, messages, alerts, and the like. For example, the system may receive data related to a prior history of interactions with the application for each user to rearrange the layout and displayed content in a way that is configured to increase future user engagement with the application.

The received data associated with previous user engagement may include metadata that may be used to determine a content layout. For example, the metadata may include home card dwell time, home card click through rate, a quantity of home cards accessed, or a combination thereof. The metadata may also include a quantity of times the user accesses the application, a quantity of home cards accessed, how long the home cards are accessed, a total time in the application, or a combination thereof. It is to be understood that these metrics and types of metadata are provided as examples and other forms of metadata or measurable metrics that indicate user engagement may also be used.

In some implementations, aspects of the present disclosure may rank home cards (e.g., user interface features) and content within the home cards to optimize user engagement, personalize the application display based on previous user engagement by the user with the home cards, and optimize a user's overall health. In such cases, the computing devices of the present disclosure may determine a content layout based on information associated with the user, previous user engagement, the user's profile preferences, received physiological data associated with the user, or a combination thereof.

For example, the system may highlight (e.g., make larger, use a color that stands out, arrange towards the top of a view) home cards or other visual components of interest to the user based on the physiological data and the received data associated with previous user engagement while also minimizing the size of or otherwise visually deemphasizing the home cards of less interest. In such cases, the system may improve product experience, tailor the experience to the user, and may increase user engagement with the application. For example, if the user is an athlete, then the determined content layout of the home cards may be tailored to activity and athletic performance. In another example, if the user is interested in tracking fertility patterns, then the determined content layout of the home cards may be tailored to body temperature and related physiological data. In such cases, the system may change the layout (e.g., order, size, ranking, and the like) of the home cards and/or content within the home cards in order to best serve the user for their individual preferences and needs.

The system may learn and optimize the ability to predict the optimal content and content layout displayed to the user to maximize user engagement based on a defined optimization target or set of optimization targets. In such cases, the user may be able to receive consistent insights every time the user accesses the application to support habit-formation and track progress over time. In some cases, users may view new insights and new content as time progresses, and view their daily insights in an updated manner based on the determined content layout. In some implementations, the system may be designed to learn and improve accuracy as the user accesses the determined content layout. For example, the system may increase the value and accuracy of the content of the application associated with the wearable device by making every interaction with the user interface features more personal, engaging, and actionable. The system may optimize the user experience such that increased user engagement with the application may increase the health and wellness of the user.

Aspects of the disclosure are initially described in the context of systems supporting physiological data collection from users via wearable devices. Additional aspects of the disclosure are described in the context of systems and example graphical user interfaces (GUIs). Aspects of the disclosure are further illustrated by and described with reference to apparatus diagrams, system diagrams, and flowcharts that relate to techniques for application personalization.

FIG. 1 illustrates an example of a system 100 that supports techniques for application personalization in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light emitting diodes (LEDs) (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols.

Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for application personalization. In particular, the system 100 illustrated in FIG. 1 may support techniques for analyzing user engagement for users 102, and configuring a content layout of a user interface based on received physiological data and previous user engagement. For example, as shown in FIG. 1, User 1 (e.g., user 102-*a*) may be associated with a wearable device (e.g., ring 104-*a*) and a user device 106-*a*. In this example, the ring 104-*a* may collect physiological data associated with the user, including temperature, heart rate, HRV, and the like. In some aspects, the user device 106-*a* may receive the physiological data and data associated with previous user engagement by the user 102-*a* with user interface features of an application running on user device 106-*a* associated with the wearable device (e.g., ring 104-*a*). The application associated with the ring 104-*a* may be configured to process and display the physiological data received from the ring 104-*a* to the user via the user device 106-*a*.

Techniques for application personalization may be performed by any of the components of the system 100, including the ring 104-*a*, the user device 106-*a* associated with User 1, the one or more servers 110, or any combination thereof. The system 100 may be configured to receive physiological data, receive previous indications of interactions, and change the layout of the application home screen (e.g., including the user interface features) to accommodate the user and their needs. For example, the system 100 may determine a content layout of the user interface features within the application associated with the ring 104-*a* based on an output of a predictive model. The predictive model may be configured to increase future user engagement with the user interface features based on the received data associated with previous user engagement. In some cases, the predictive model may use at least the received physiological data as an input. The system 100 may cause a GUI of the user device 106-*a* to display the determined content layout of the user interface features.

In some implementations, the system 100 may determine an order to display the user interface features, determine a ranking of the user interface features, and/or determine a size of the user interface features based on the physiological data and the received data associated with previous user engagement. In such cases, the system 100 may determine the content layout based on the order, ranking, and/or size. For example, if the system 100 receives indications that the user 102-*a* is an athlete, the system 100 may determine a content layout based on previous user engagement with the user interface features and the received physiological data. For example, the user 102-*a* may interact with user interface features of the application associated with activity multiple times a day, and the content layout may be updated to display the user interface features associated with activity.

In such cases, the system 100 may configure the GUI to display the user interface features associated with activity in a greater size (or otherwise visually highlight these features) than user interface features associated with sleep or the like. The system 100 may configure the GUI to display the user interface features associated with activity at the top of the application home screen such that when the user 102-*a* accesses (e.g., opens) the application, the activity goal and metrics of interest to the user may be displayed and emphasized. The content layout may be determined based on a quantity of times and/or a duration that the application is accessed, a quantity of times and/or a duration that the user interface features (e.g., associated with activity) are accessed or interacted with, or a combination thereof.

In some implementations, the system 100 may determine media content associated with the user interface features within the application based on the physiological data and the received data associated with previous user engagement. In some implementations, the system 100 may generate alerts, messages, or recommendations for User 1 (e.g., via the ring 104-*a*, user device 106-*a*, or both) based on the physiological data and the received data associated with previous user engagement. For example, the system 100 may display a recommended video (e.g., a training or educational video) associated with the physiological data or a recommended audio (e.g., a meditation or educational recording) associated with the physiological data for the user 102-*a*.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
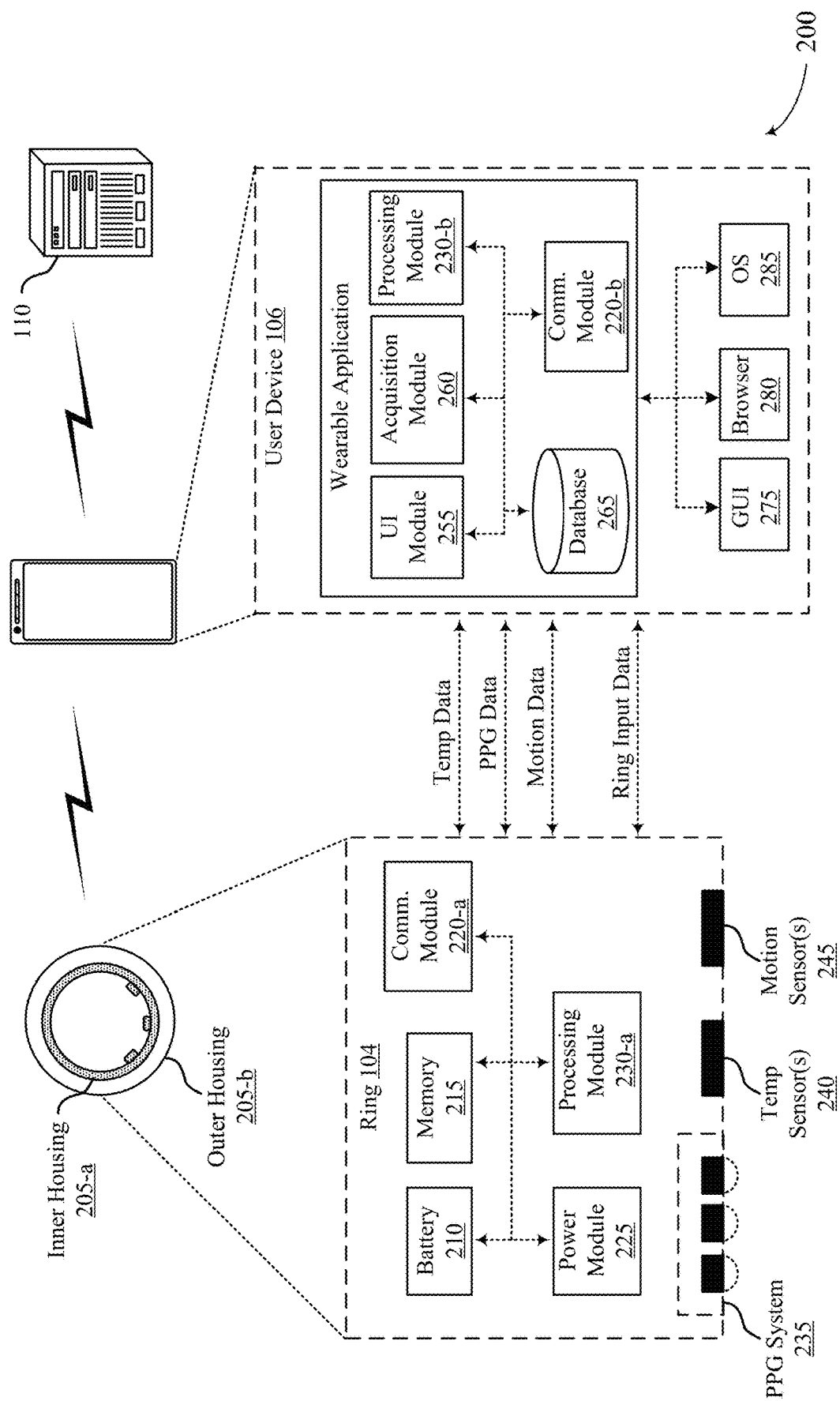
FIG. 2 illustrates an example of a system that supports techniques for application personalization in accordance with aspects of the present disclosure.

FIG. 2 illustrates an example of a system 200 that supports techniques for application personalization in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG LEDs. In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits).

The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, that may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 that the optical receiver(s) receive transmitted light that is reflected through the region of the user's finger. In some implementations, the PPG system 235 may be configured as a transmissive PPG system 235 that the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include LEDs. The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and Readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for application personalization. In particular, the respective components of the system 200 may be used to determine a content layout of the user interface features within the application associated with the wearable device (e.g., ring 104) based on the received data associated with previous user engagement and other factors (e.g., measured physiological data from a user). For example, the system 200 may receive physiological data from the wearable device associated with the user and receive data associated with previous user engagement by the user with user interface features of the application. The content layout may be determined based on a predictive model configured to increase future user engagement with the user interface features.

For example, as noted previously herein, the ring 104 of the system 200 may be worn by a user to collect data from the user, including temperature, heart rate, motion, and the like. The ring 104 of the system 200 may collect the physiological data from the user based on arterial blood flow. The physiological data may be collected continuously. In some implementations, the processing module 230-*a* may sample the user's physiological data continuously throughout the day and night. Sampling at a sufficient rate (e.g., one sample per second or per minute) throughout the day may provide sufficient data for analysis described herein. Data collected by the ring 104 may be used to cause the GUI of the user device to display the determined content layout of the user interface features (e.g., including the physiological data), that may be further shown and described with reference to FIG. 4.

Figure 3:
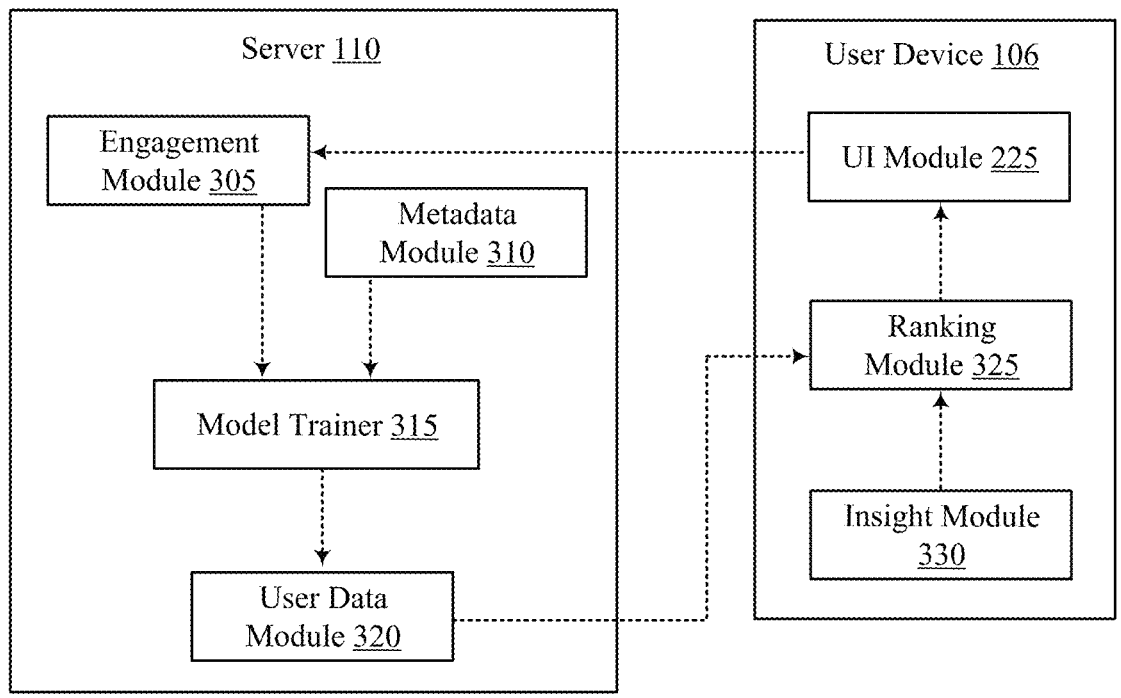
FIG. 3 illustrates an example of a system that supports techniques for application personalization in accordance with aspects of the present disclosure.

FIG. 3 illustrates an example of a system 300 that supports techniques for application personalization in accordance with aspects of the present disclosure. The system 300 may implement, or be implemented by, system 100 or system 200. In particular, system 300 illustrates an example of a user device 106 and a server 110, as described with reference to FIG. 1.

The user device 106 of the system 300 may be communicatively coupled to server 110 via wired or wireless communication protocols. For example, the user device 106 may be communicatively coupled to the server 110 via a network. The server 110 may include an engagement module 305, a metadata module 310, a model trainer 315, and a user data module 320. The user device 106 may include a UI module 255, a ranking module 325, and an insight module 330. The system 300 may be configured to receive physiological data, receive previous indications of interactions, and configure the content layout of the user interface features displayed on an application running on user device 106. In some examples, some or all of the modules illustrated within server 110 may instead be running within the user device 106 and/or within the wearable device (e.g., ring 104).

In some implementations, the engagement module 305 may receive, via the user device 106, data associated with previous user engagement by the user with user interface features of an application. The user interface features of the application may be associated with a wearable device (e.g., ring 104) and configured to display content to the user. For example, the user interface features may include cards, tiles, insights, messages, alerts, and the like. In some cases, the engagement module 305 may receive, via the user device 106, indications of user engagement with the user interface features of the determined content layout based on causing the GUI of the user device 106 to display the determined content layout via UI module 255.

The engagement module 305 may receive engagement signals for user interface features based on a user's application access time, scroll patterns, or both. In such cases, the engagement module 305 may receive an engagement signal based on a user viewing (e.g., reading) the user interface feature in the absence of active feedback (e.g., a click-through). The engagement signal may be an example of a signal generated by supervised learning to optimize user engagement. In some implementations, the engagement module 305 may receive engagement history associated with the user to predict a future engagement pattern. In some cases, the engagement module 305 may estimate a probability of engagement by the user with each user interface feature of the application and transmit the probability to the ranking module 325.

The metadata module 310 may determine metadata of the received data associated with previous user engagement. For example, the metadata may include a quantity of times the application is accessed, a quantity of user interface features accessed, an indication of which user interface feature is accessed, a duration of time that the user accesses the application, a duration of time that the user accesses a user interface feature, a time of day that the user accesses the application, a time of day that the user accesses the user interface feature, or a combination thereof. For example, the metadata module 310 may determine that the user accesses sleep stories (e.g., user interface feature) at 11 PM and not 11 AM. In other examples, the metadata module 310 may determine that the user accesses the Activity Score multiple times a day while the user accesses the Readiness Score once a day.

In some cases, the metadata module 310 may determine metadata associated with media content of the determined content layout. For example, the metadata module 310 may determine variations in media content that may result in a confirmed response from the user (e.g., the user accesses the determined content). In some cases, the metadata module 310 may determine a messaging tone associated with the media content (e.g., active, motivational, passive, celebratory, directive, neutral, and the like). The variations of media content may be an example of different presentations of the same media content. For example, the system 300 may cause the GUI to display an educational video including media content or an audio message including the same media content. In such cases, the system 300 may optimize the media content and the presentation of the media content independently.

The metadata module 310 may receive metadata associated with the user (e.g., user demographics, user type, device type, user tenure, onboarding goals, and the like). In some cases, the metadata module 310 may receive metadata associated with the physiological data (e.g., how much sleep the user had last night, heart rate, temperature, HRV, and the like). In some implementations, the metadata module 310 may receive metadata associated with the media content (e.g., content genre, content subgenre, tone, medium, length, target expertise, and the like). In some examples, the medium may include audio, video, illustration, or a combination thereof. In such cases, the metadata module 310 may determine metadata tailored to the user experience in order to maximize user engagement. For example, the determined content layout may be based on determining the metadata.

The metadata module 310 may receive physiological data from a wearable device associated with a user. The physiological data may include a user's health history, health and/or wellness state, how much the user has been sleeping and/or exercising, the user's Readiness Score, Sleep Score, Activity Score, and the like. The physiological data may also include body temperature, heart rate, HRV, blood oxygen concentration, and the like. In some cases, the metadata module 310 may determine that the physiological data from the wearable device associated with the user satisfies one or more thresholds. In some cases, the system 300 may display the content associated with the physiological data that satisfies the threshold at the top of the application home screen independently of the ranking system, as described further with reference to FIG. 4.

The metadata, physiological data, or both may also be an example of a signal generated by supervised learning to optimize the user's overall health. For example, the layout of the GUI may be optimized to increase or maintain the health of the user, as measured by physiological data such as HRV, resting HR, activity metrics, sleep metrics, or a combination thereof. In such cases, the GUI may be optimized over time based on the received physiological data to optimize (e.g., improve) the user's overall health. A predictive model may be trained to arrange the GUI in such a way to optimize user engagement and improve the health of the user.

The model trainer 315 may determine a content layout of the user interface features within the application associated with the wearable device based on an output of a predictive model and/or other sources of information pertaining to the user or content. The predictive model may be an example of the model trainer 315. For example, the model trainer 315 may be configured to increase future user engagement with the user interface features based on the received data associated with previous user engagement. In some implementations, the model trainer 315 may determine an updated content layout of the user interface features within the application based on the predictive model output and the received indications of user engagement with the user interface features of the determined content layout.

The model trainer 315 may use at least the received physiological data as input. For example, the model trainer 315 may input the physiological data into a machine learning classifier. In some cases, the model trainer 315 may be used to train the machine learning classifier. In some cases, the model trainer 315 may use matrix factorization, latent Dirichlet allocation, Factorization Machines algorithms (e.g., lightFM) (or other similar recommendation models), neural/deep learning approaches, or a combination thereof. For example, the model trainer 315 may use lightFM weekly on a random sample of users. In some cases, time-varying signals such as scores and biometrics (e.g., physiological data) may be included in the matrix factorization. For example, the model trainer 315 may include neural collaborative filtering to learn personal preferences associated with the time-varying signals. The model trainer 315 may include a fold-in that is run daily on all users with activity for the corresponding day. In some implementations, the model trainer 315 may learn a latent vector representation of user preference in which each dimension represents a media content topic (e.g., sleep sounds, guided meditations, education content of varied topic, and the like).

In some implementations, the model trainer 315 may implement supervised learning. For example, each user engagement with the application associated with the wearable device may train the model trainer 315 to generate relevant content and insights for the user. In such cases, the user may have a sense that the system 300 may be "getting to know them" as the user passively or actively interacts with the application over time. The supervised learning may include item-based optimization, joint/feed-based optimization, or both. For example, the item-based optimization may estimate a probability of engagement by the user with each piece of content (e.g., user interface feature) and construct the feed (e.g., content layout) by ranking by the probabilities via ranking module 325. The model trainer 315 may generate a full candidate feed and estimate a total engagement based on the join/feed-based optimization.

The system 300 may precompute the user interface features to be displayed in the GUI. In such cases, the system 300 may disregard a time of day the user accesses the application but rather precomputes multiple feeds for different parts of the calendar day relative to the user's wake time and bedtime. The system 300 may store the precomputed data in a storage component of the server 110. By precomputing the user interface features to be displayed, the system 300 may experience a reduced latency and improved processing times such that the user interface features may be displayed in the determined content layout at the time of accessing the application.

In some examples, the model trainer 315 may use time of day to train the model and determine the content layout. For example, the user may have different goals when opening the application at different times of day. In some cases, the time of day may be based on the user's personal day rather than a calendar day. For example, a user who wakes up at 6 AM may receive different content and/or goals at 10 AM as compared to a user that wakes up at 10 AM. In other examples, a user who goes to sleep at 9 PM may receive different content and/or goals at 8 PM as compared to a user that goes to sleep at 12 AM. In such cases, the system 300 may display relevant content for the morning and/or evening relative to the user's individual day because the system 300 may know when the user is asleep or awake rather than displaying content based on a calendar day.

In one example, the user may check the Sleep Score in the morning, listen to a sleep story before bed, or check the activity goals after a workout. In such cases, different tags or content may be relevant at different times of the day. The system 300 may promote different cards (e.g., content) based on time of day and/or unmet goals. For example, the system 300 may de-emphasize (e.g., hide or move to the bottom of the application page) activity metrics if user is approaching bedtime. In another example, the system 300 may move activity content to the top of the application page if the user has not achieved the activity goal or move a card about taking a restful moment to the top of the application page if the user has been too active. Allowing a continuous time predictor may increase the complexity of the system 300, and in such cases, the system 300 may not precompute recommendations but may learn arbitrary associations. For example, the ability to build patterns and trends to communicate back to the user may be based on the ability to gather data over arbitrary periods of time.

The model trainer 315 may use a sequence to train the model and determine the content layout. In one example, the system 300 may display an introduction card followed by educational video content on how to use the application the first time the user accesses the application. As the user continues to access the application, the system 300 may display content such as insights-driven programs and challenges that may be relevant to the user. In such cases, the system 300 may use a collaborative filtering mechanism such that the model trainer 315 may learn common patterns of behavior associated with the user. For example, if the system 300 predicts that the user may watch videos in a certain order regardless of how the videos may be presented, the model trainer 315 may learn to suggest the videos in the certain order (e.g., sequence). In other examples, the system 300 may display a certain video after the user watches the preceding video in the sequence.

The model trainer 315 may include a representation of items that may indicate whether the items are user interface features or media content of the user interface features. The model trainer 315 may periodically refresh and recreate the representation of items based on the predictive model. In some cases, the model trainer 315 may include a representation of users. In such cases, the model trainer 315 may transmit the representation of items and the representation of users to the user data module 320.

In some implementations, the user data module 320 may receive the representations from the model trainer 315 and transmit the representation of items and representation of users to the user device 106. In such cases, the user device 106 may calculate an affinity between the representation of items and representation of users. For example, the user device 106 may calculate a ranked representation via ranking module 325.

The ranking module 325 may calculate an output (e.g., ranking) between the representation of items and representation of users. For example, the ranking module 325 may calculate a dot product between the representation of items and representation of users for each user interface feature. In some examples, the ranking module 325 may rank the result of the dot product and generate a ranked list. In such cases, the ranking module 325 may transmit the ranked list to the UI module 255.

In some cases, the ranking module 325 rank the content of each user interface feature each time the application is accessed (e.g., opened). For example, the ranking module 325 may calculate a ranking at the time the application is opened. In other examples, the model trainer 315 may precompute the ranking. In such cases, the user may access the application, and the model trainer 315 may transmit the precomputed user interface features and ranking of the precomputed user interface features in response to accessing the application. The ranking module 325 may be trained periodically via the model trainer 315 using engagement data received from the engagement module 305. In such cases, the parameters of the model trainer 315 may be transmitted to the user device 106 where the ranking module 325 may determine card scoring and final ranking on the user device 106.

In some implementations, the ranking module 325 may optimize user engagement and select content to construct the home feed (e.g., application home screen). In some cases, the engagement module 305 may generate an engagement probability for the content, and the ranking module 325 may use the probability to filter and prioritize the content. The content may be an example of insights, patterns, rewards, suggested tags, programs, challenges, guided audio sessions, educational videos, push notifications, emails, library content, or a combination thereof. In such cases, the ranking module 325 may determine a ranking of the user interface features based on the physiological data and the received data associated with previous user engagement. For example, the ranking module 325 may rank user interface features and media content within the user interface features to optimize user engagement and/or optimize the user's overall health. In some cases, the ranking module 325 may identify user interface features that may be displayed at the top of the application home screen regardless of the ranking.

In some implementations, the ranking module 325 may determine an order to display the user interface features based on the physiological data and the received data associated with previous user engagement. For example, the ranking module 325 may determine the order of the user interface features on the application home screen by predicting which user interface features may be most likely to be engaged with. In some cases, the system 300 may determine the content layout based on determining the order. The system 300 may determine the order based on determining the ranking. In some examples, the system 300 may determine a size of the user interface features based on the physiological data and the received data associated with previous user engagement where determining the content layout is based on determining the size.

The system 300 may determine one or more presentation variants of the user interface features based on the physiological data and the received data associated with previous user engagement. For example, the system 300 may determine the size of the user interface features, text details of the user interface features, graphical features of the user interface features, abbreviated details of the user interface features, or a combination thereof. For example, the system 300 may determine that a larger home card may include an increased level of detail in the text, additional graphs, or both. In other examples, the system 300 may determine that a smaller home card may include abbreviated content (e.g., text, graphs, etc.), be reduced to a title with a "click to expand" user interface element, or both.

The ranking module 325 may assign a score to each item such that the user interface features may be displayed in an order corresponding to the score. For example, a user interface feature assigned to a higher score may be displayed towards the top of the application page as compared to a user interface feature with a lower score. In some implementations, the ranking module 325 may score sets of multiple user interface features (e.g., together with an individual user interface feature scores) to construct the display jointly. For example, the ranking module 325 may assign a higher score to user interface features such as workout videos for a user as compared to user interface features associated with sleep. The system 300 may display the user interface features based on the score of each user interface feature, the metadata associated with each user interface feature, and/or machine-learned representations (e.g., embeddings) that describe the user interface features already displayed on the application page to reduce the redundancy.

The insight module 330 may transmit candidate items to the ranking module 325. For example, the insight module 330 may generate a set of candidate cards that may be ranked by the ranking module 325. In some cases, the insight module 330 may run Waltari rules. In some implementations, the insight module 330 may determine media content associated with the user interface features within the application based on the physiological data and the received data associated with previous user engagement. The content layout may be determined based on determining the media content. The media content may include a recommended video associated with the physiological data, a recommended audio associated with the physiological data, a request to input symptoms associated with the physiological data, a pattern detected from the physiological data, a confirmation of the physiological data, a suggested tag associated with the physiological data, or a combination thereof.

The UI module 255 may receive the ranked list from the ranking module 325. In some cases, the UI module 255 may transmit segment or amplitude information to the engagement module 305. In some examples, the UI module 255 may cause a GUI of the user device 106 to display the determined content layout of the user interface features. In some implementations, the UI module 255 may cause the GUI of the user device 106 to display an alert based on determining that the physiological data satisfies the one or more thresholds. In such cases, the determined content layout includes the alert. The UI module 255 may cause the GUI of the user device 106 to display a message based on determining that the physiological data satisfies the one or more thresholds. In such cases, the determined content layout includes the message. The system 300 may be able to reorder the user interface features based on the ranking algorithm to optimize each user's application home screen to display the most relevant user interface features, as described further with reference to FIG. 4.

Figure 4:
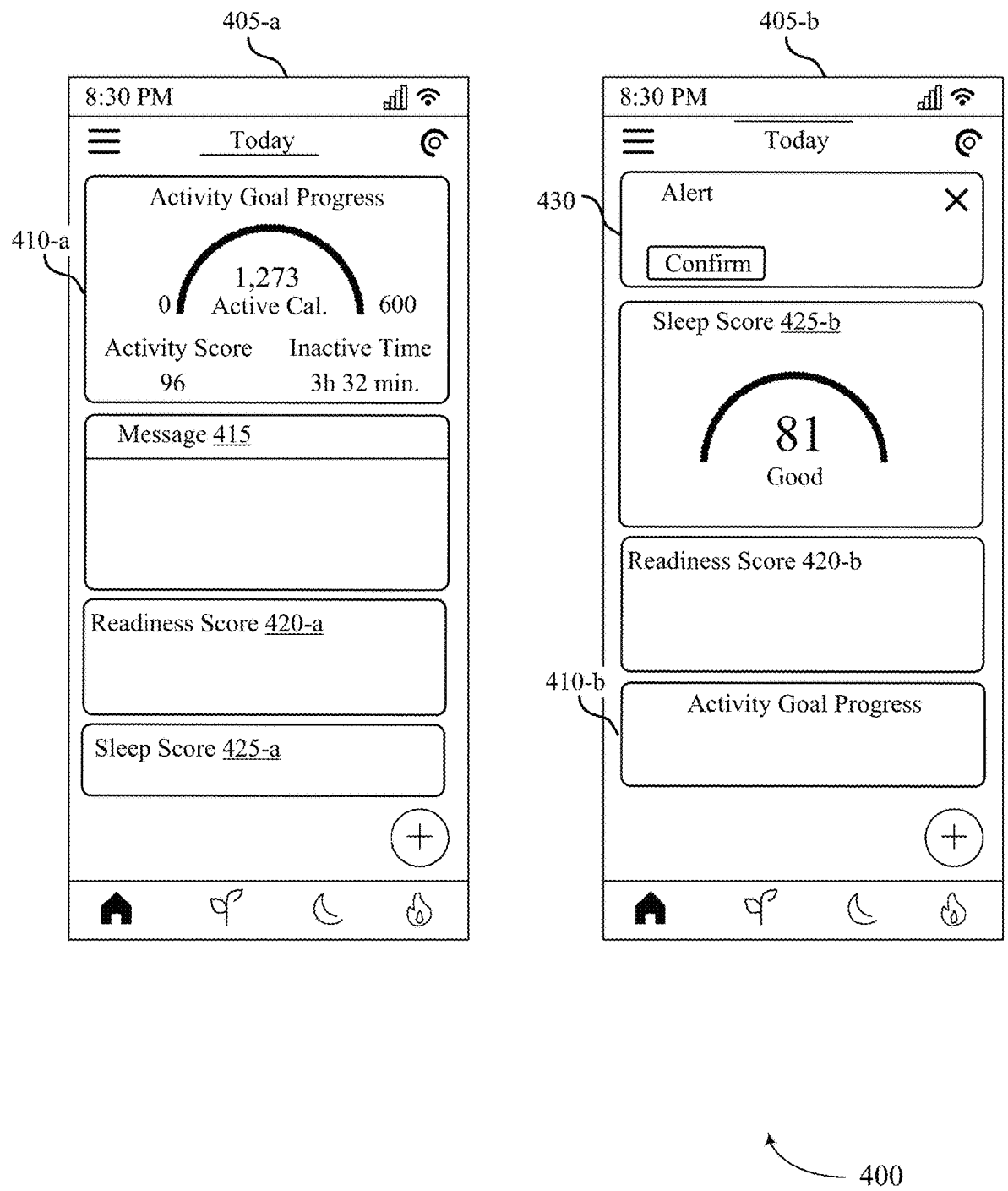
FIG. 4 illustrates an example of a graphical user interface (GUI) that supports techniques for application personalization in accordance with aspects of the present disclosure.

FIG. 4 illustrates an example of a GUI 400 that supports techniques for application personalization in accordance with aspects of the present disclosure. The GUI 400 may implement, or be implemented by, aspects of the system 100, system 200, system 300, or any combination thereof. For example, the GUI 400 may be an example of a GUI 275 of a user device 106 (e.g., user device 106-a, 106-b, 106-c) corresponding to a user 102.

In some examples, the GUI 400 illustrates a series of application pages 405 that may be displayed to a user 102 via the GUI 400 (e.g., GUI 275 illustrated in FIG. 2). The server 110 of system 200 may cause the GUI 400 of the user device 106 (e.g., mobile device) to display the determined content layout (e.g., via application page 405-a or 405-b). In such cases, the system 300 may output the determined content layout on the GUI 275 of the user device 106-a to indicate determined content layout for user 102-a and may output a different determined content layout on the GUI 275 of the user 102-b to indicate the different determined content layout for user 102-b.

Continuing with the example above, upon determining a content layout of the user interface features within the application associated with the wearable device, the user 102 may be presented with the application page 405-a or application page 405-b upon opening the wearable application 250. As shown in FIG. 4, the application pages 405 may include activity goal progresses 410, message 415, Readiness Scores 420, Sleep Scores 425, an alert 430, or a combination thereof. The activity goal progresses 410, message 415, Readiness Scores 420, Sleep Scores 425, and alert 430 may be an example of user interface features.

The system 300 may determine the content layout of application page 405-a and application page 405-b to increase future user engagement with the user interface features. For example, the system 300 may be configured to improve the application home screen (e.g., displayed via application page 405-a and application page 405-b) based on the health context of the user, time of day the user accesses the application pages 405, data associated with previous user engagement by the user, physiological data associated with the user, or a combination thereof. In some cases, the system 300 may be configured to improve the application home screen (e.g., displayed via application page 405-a and application page 405-b) based on user data and user preferences. Improving the application home screen may improve the user engagement experience as well as improving the health of the user over time. The system 300 may transmit a notification (e.g., message 415 or alert 430) based on the user input data and/or user input preferences. For example, the system 300 may determine the content layout of application page 405-a and application page 405-b based on the state of the user (e.g., if the user is waking up, resting, exercising, going to bed, and the like.)

In some examples, the system 300 may generate the determined content layout based on an output of a predictive model and/or other sources of information pertaining to the user or content. In such cases, the system 300 may display content the user may most engage with while also considering other factors such as ensuring consistency of content in the user interface, maximizing relevance of the content to independently determined health conditions or goals, and removing excess redundancy of content. For example, the system 300 may determine an order to display the user interface features, a ranking of the user interface features, and/or a size of the user interface features based on the physiological data and the received data associated with previous user engagement. In such cases, the system 300 may determine which user interface features are displayed via the application pages 405, the order that the user interface features are displayed, the content within the user interface features, or a combination thereof.

In some cases, the system 300 may determine an order to display the user interface features and filter the user interface features simultaneously. For example, the system 300 may determine which user interface features may be displayed and the order of the determined user interface features to be displayed simultaneously. In such cases, the system 300 may select the N highest-ranked user interface features in an ordering to display. In some implementations, the system 300 may determine which user interface features are to be displayed by applying a threshold criterion to a score associated with each user interface feature.

In some cases, the application page 405-*a* may be associated with a user 102 interested in activity metrics. For example, the system 300 may determine that the user is interested in activity metrics based on received physiological data indicating that the user is highly active or has recently increased activity levels and/or received data associated with previous user engagements by the user with the user interface features of the application page 405-*a*. In such cases, the previous user engagements may be examples of a user selecting the activity goal progress 410-*a* every time the application page 405-*a* opens (e.g., multiple times a day), a user viewing the activity goal progress 410-*a* while scrolling through the application page 405-*a* (e.g., without clicking on the activity goal progress 410-*a*), or other interactions with the activity goal progress 410-*a*. The system 300 may display the activity goal progress 410-*a* first (e.g., at the top of the application page 405-*a*) when the application page 405-*a* is accessed. In some cases, the size of the activity goal progress 410-*a* may be larger than the Readiness Score 420-*a* and/or the Sleep Score 425-*a*.

Based on the system 300 identifying that user 102 is an athlete or interested in activity metrics, the system 300 may display the activity goal progress 410-*a* in a higher order ranking than for a user who is less interested in activity goals. In such cases, the activity goal progress 410-*a* may include a higher ranking than the message 415, Readiness Score 420-*a*, and the Sleep Score 425-*a*. In some cases, the user engagement with the activity goal progress 410-*a* may be higher on days with higher activity such that the system 300 may display the activity goal progress 410-*a* at the top of the application page 405-*a*.

In some cases, the system 300 may display the activity goal progress 410-*a* and/or other activity metrics in a higher order ranking (e.g., at the top of the application page 405-*a*) based on the system 300 determining that the user is beginning a workout or starting to exercise. Examples of other activity metrics displayed to the user in a higher order ranking may include, but are not limited to, how many steps the user has taken, how many calories the user has burned, a guided exercise video, metrics to track a workout, the user's activity history, or a combination thereof. For example, the system 300 may determine that the user is exercising based the physiological data received by the system 300. In some examples, the system 300 may determine that the user is exercising based on a user input received by the system 300 indicating that the user started a workout, completed a workout, or both. In some cases, the system 300 may determine that the user exercises at a regular time each day (e.g., at 6 PM every Monday through Friday), and the system 300 may display the activity goal progress 410-*a* and/or other activity metrics at the top of the application page 405-*a* at that time for the determined days based on the determination.

In another example, if the user is interested in tracking fertility patterns, then the determined content layout on the application page 405-*a* may be tailored to body temperature and related physiological data. For example, the system 300 may display the activity goal progress 410-*a* and/or other activity metrics in a lower order ranking (e.g., at the bottom of the application page 405-*a* or absent from the application page 405-*a*) based on the system 300 determining that the user is interested in tracking fertility patterns. In such cases, the predictive model may use at least the received physiological data, including the user's menstrual cycle, as input to determine the content layout on the application page 405-*a*.

In some cases, the application page 405-*b* may be associated with a user 102 interested in sleep metrics. For example, the system 300 may determine that the user is interested in sleep metrics based on received physiological data indicating a need for more or better sleep and/or received data associated with previous user engagements by the user with the user interface features of the application page 405-*b*. In such cases, the previous user engagements may be an example of a user selecting the Sleep Score 425-*b* every time the application page 405-*b* opens (e.g., multiple times a day). The system 300 may display the Sleep Score 425-*b* in a higher order than the activity goal progress 410-*b* when the application page 405-*b* opens. In some cases, the size of the Sleep Score 425-*b* may be larger than the Readiness Score 420-*b* and/or the activity goal progress 410-*b*. Based on the system 300 identifying that the user 102 is interested in sleep metrics, the system 300 may display the Sleep Score 425-*b* in a higher order than for a user who is less interested in sleep metrics. In such cases, the Sleep Score 425-*b* may include a higher ranking than the Readiness Score 420-*b* and the activity goal progress 410-*b*.

The layout (e.g., order, size, or both) of user interface features of application page 405-*b* may be different than the layout of user interface features of application page 405-*b*. For example, the default view of application page 405-*a* may be different than the default view of application page 405-*b*. The system 300 may determine the content within the application pages 405 to optimize for user engagement, overall health of the user, or both. In such cases, the system 300 may change the order and/or size of user interface features on application pages 405 based on received physiological data and received indications of previous user engagement.

In some cases, the system 300 may determine a size of the user interface features such that a user interface feature of interest may be a full format (e.g., larger in size) and the user interface feature of less interest may be a compressed format (e.g., smaller in size). In such cases, the system 300 may be configured to display less information for user interface features that the user is less interested in based on the physiological data and the received data associated with previous user engagement.

As noted previously herein, physiological data collected from a user 102 may be used to calculate scores/metrics (e.g., health risk scores, Sleep Scores, Readiness Scores) for the respective user. Calculated scores/metrics may be displayed to the user 102 via a user device 106 corresponding to the user 102 based on the determined content layout.

The server 110 of system may cause the GUI 400 of the user device 106 to display a message 415 (e.g., insights). In some implementations, the user device 106 and/or servers 110 may generate messages 415 that may be displayed to the user 102 via the GUI 400. The system 300 may display the message 415 to the user 102 if a user's data satisfies a threshold. For example, if a user's total sleep time for a given timeframe drops into an unhealthy range (e.g., below the threshold), the system 300 may send a message 415 to the user.

In some implementations, the content layout may be determined based on the user's data satisfying the threshold. For example, the system 300 may configure the GUI 400 to display on the application page 405-a where the message 415 is a higher priority (e.g., located towards the top of the application page 405-a). In such cases, the message 415 may be larger in size compared to the Readiness Score 420-a and the Sleep Score 425-a. The larger size may account for the message 415 including more details (e.g., text, graphics, unabbreviated content, and the like) compared to the Readiness Score 420-a and the Sleep Score 425-a. In some examples, the message 415 may be displayed towards the top of the application page 405-a regardless of the ranking compared to the other user interface features.

The messages 415 may include additional information associated with physiological data associated with the user. For example, the message 415 may include a link to an external document, a survey, medical guidance, or any combination thereof. The message 415 may inform the user that their physiological data is normal or abnormal and, if abnormal, may provide health guidance as to a list of steps that the user 102 may do to improve their overall health.

The server 110 may transmit a message 415 to the user to be displayed on application page 405-a, where the message 415 is associated with a potential health risk for the user. For example, the user may receive message 415, that may indicate for the user to check in with a contact person associated with a group of users (e.g., administrator of an office). In some other cases, the user may receive message 415, that may prompt the user to check in for more information or dismiss the message 415. The messages 415 may be configurable/customizable, such that the user may receive different messages 415 based on different health risk scores.

In some implementations, the user device 106 and/or servers 110 may generate alerts 430 that may be displayed to the user via the GUI 400. In some cases, the system 300 may indicate to the administrator (e.g., via the administrator user device 106-d) whether the user confirmed, viewed, and or dismissed the alert 430. In some cases, the system 300 may generate an alert 430 on the application page 405-b when a user's data satisfies some threshold. For example, if a user's total sleep time for a given timeframe drops into an unhealthy range (e.g., below the threshold), the system 300 may generate an alert 430 for the user. In some cases, the message 415 may provide a recommendation such as "Here is a link to an article for some tips and tricks to getting a better night's sleep."

In some examples, the alert 430 may be able to notify the user 102 if a metric (e.g., Sleep, Readiness, or Activity Score) is out of range. In such cases, the alert 430 may serve as an accountability driver such that when the user 102 opens the application platform, the GUI 400 may display an alert 430 such as "Hey! We notice your Sleep Score is lower than average." In some cases, the user 102 may acknowledge the alert 430.

In some implementations, the content layout may be determined based on the user's data satisfying the threshold. For example, the system 300 may configure the GUI 400 to display on the application page 405-b where the alert 430 is a higher priority (e.g., located towards the top of the application page 405-b). In such cases, the alert 430 may be larger in size compared to the Readiness Score 420-a and the activity goal progress 410-b. For example, the alert 430 may be displayed towards the top of the application page 405-a regardless of the ranking compared to the other user interface features.

Figure 5:
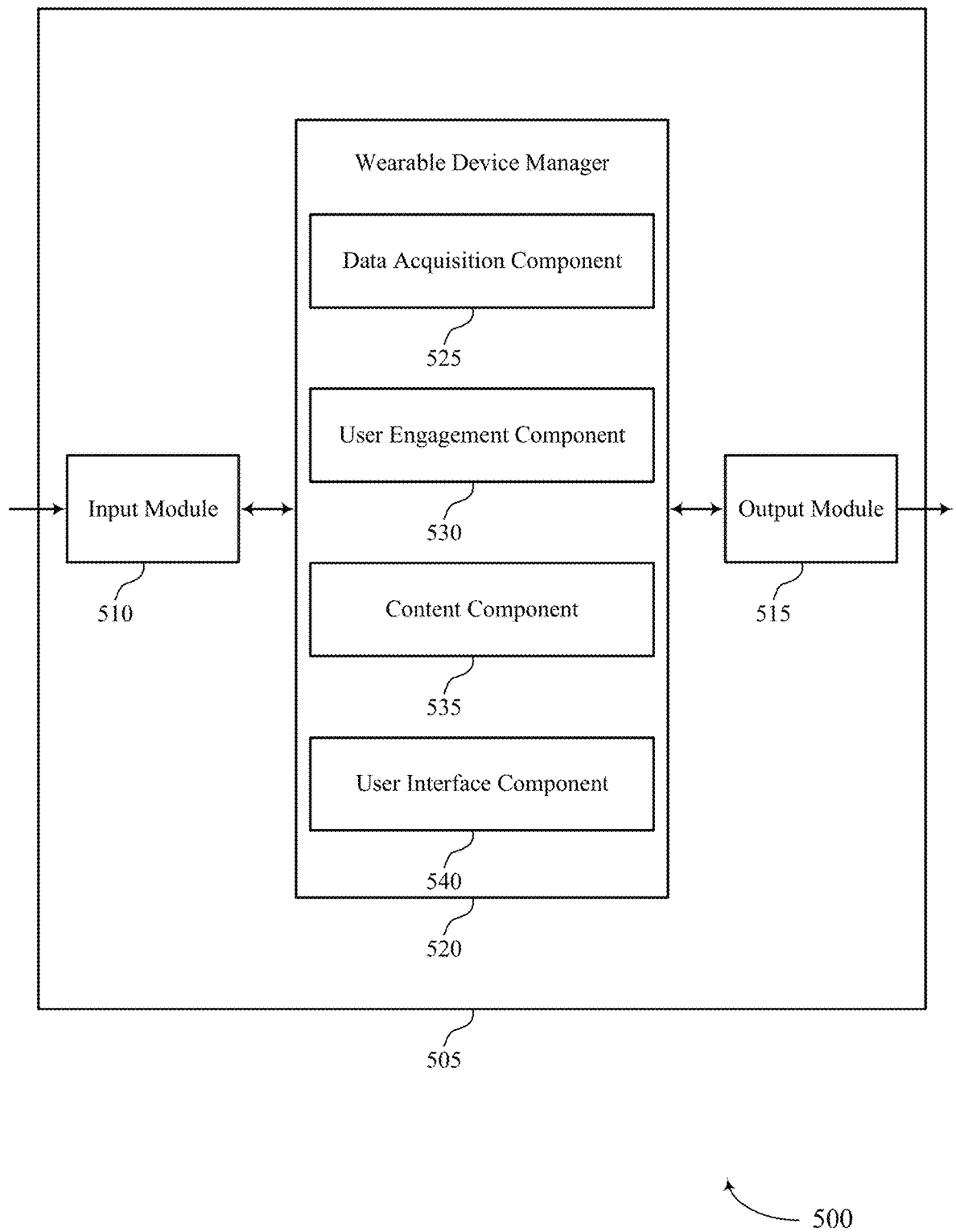
FIG. 5 shows a block diagram of an apparatus that supports techniques for application personalization in accordance with aspects of the present disclosure.

FIG. 5 shows a block diagram 500 of a device 505 that supports techniques for application personalization in accordance with aspects of the present disclosure. The device 505 may be an example of a server, a user device, a wearable device, or some combination of components from these devices. The device 505 may include an input module 510, an output module 515, and a wearable device manager 520. The device 505 may also include a processor. Each of these components may be in communication with one another (e.g., via one or more buses).

The input module 510 may provide a means for receiving information such as packets, user data, control information, or any combination thereof associated with various information channels (e.g., control channels, data channels, information channels related to illness detection techniques). Information may be passed on to other components of the device 505. The input module 510 may utilize a single antenna or a set of multiple antennas.

The output module 515 may provide a means for transmitting signals generated by other components of the device 505. For example, the output module 515 may transmit information such as packets, user data, control information, or any combination thereof associated with various information channels (e.g., control channels, data channels, information channels related to illness detection techniques). In some examples, the output module 515 may be co-located with the input module 510 in a transceiver module. The output module 515 may utilize a single antenna or a set of multiple antennas.

For example, the wearable device manager 520 may include a data acquisition component 525, a user engagement component 530, a content component 535, a user interface component 540, or any combination thereof. In some examples, the wearable device manager 520, or various components thereof, may be configured to perform various operations (e.g., receiving, monitoring, transmitting) using or otherwise in cooperation with the input module 510, the output module 515, or both. For example, the wearable device manager 520 may receive information from the input module 510, send information to the output module 515, or be integrated in combination with the input module 510, the output module 515, or both to receive information, transmit information, or perform various other operations as described herein.

The data acquisition component 525 may be configured as or otherwise support a means for receiving physiological data from a wearable device associated with a user. The user engagement component 530 may be configured as or otherwise support a means for receiving, via a user device associated with the user, data associated with previous user engagement by the user with user interface features of an application associated with the wearable device, wherein the application associated with the wearable device is configured to process and display the physiological data received from the wearable device to the user via the user device. The content component 535 may be configured as or otherwise support a means for determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input. The user interface component 540 may be configured as or otherwise support a means for causing a graphical user interface of the user device to display the determined content layout of the user interface features.

Figure 6:
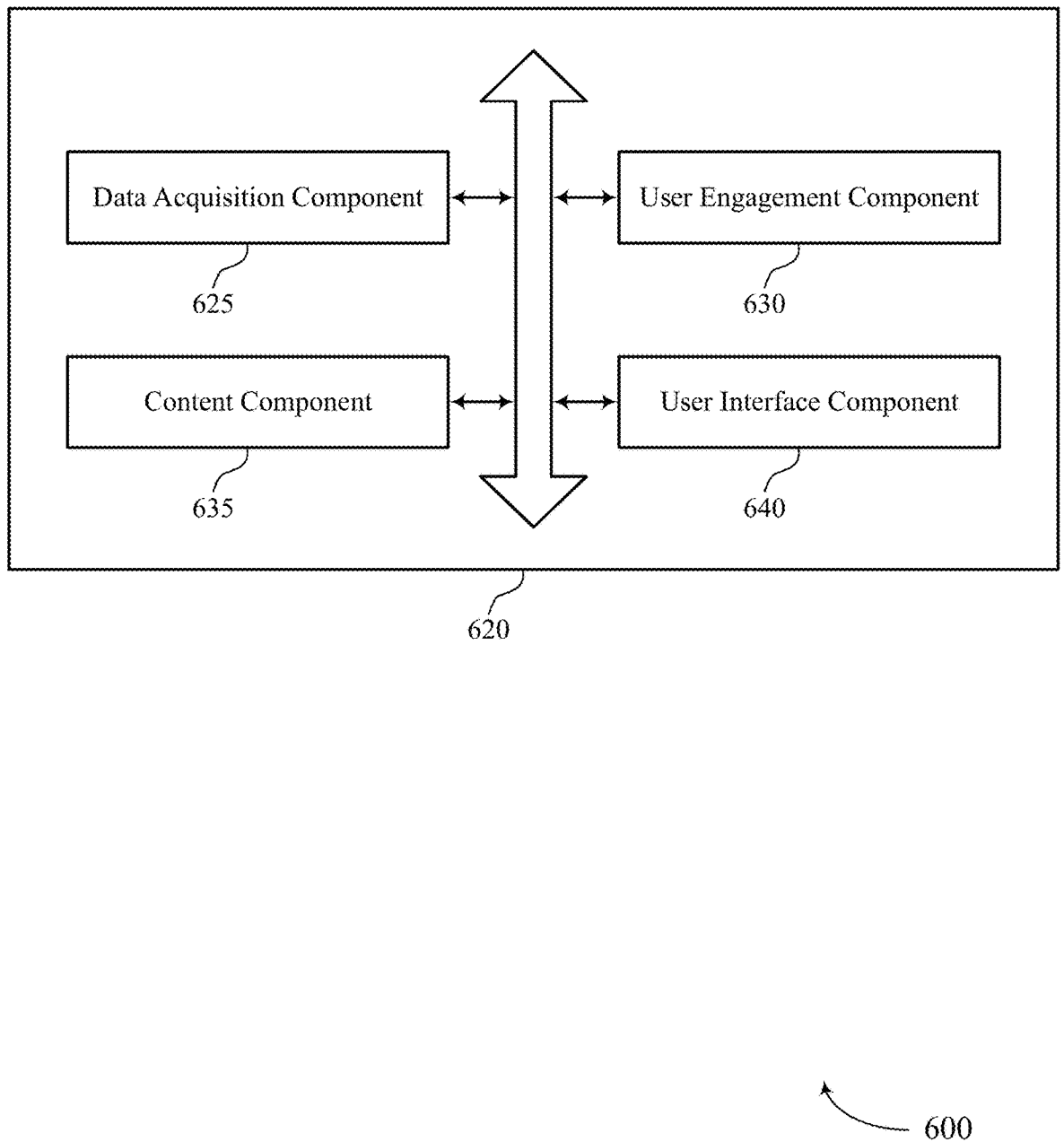
FIG. 6 shows a block diagram of a wearable device manager that supports techniques for application personalization in accordance with aspects of the present disclosure.

FIG. 6 shows a block diagram 600 of a wearable device manager 620 that supports techniques for application personalization in accordance with aspects of the present disclosure. The wearable device manager 620 may be an example of aspects of a wearable device manager or a wearable device manager 520, or both, as described herein. The wearable device manager 620, or various components thereof, may be an example of means for performing various aspects of techniques for application personalization as described herein. For example, the wearable device manager 620 may include a data acquisition component 625, a user engagement component 630, a content component 635, a user interface component 640, or any combination thereof. Each of these components may communicate, directly or indirectly, with one another (e.g., via one or more buses).

The data acquisition component 625 may be configured as or otherwise support a means for receiving physiological data from a wearable device associated with a user. The user engagement component 630 may be configured as or otherwise support a means for receiving, via a user device associated with the user, data associated with previous user engagement by the user with user interface features of an application associated with the wearable device, wherein the application associated with the wearable device is configured to process and display the physiological data received from the wearable device to the user via the user device. The content component 635 may be configured as or otherwise support a means for determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input. The user interface component 640 may be configured as or otherwise support a means for causing a graphical user interface of the user device to display the determined content layout of the user interface features.

In some examples, the content component 635 may be configured as or otherwise support a means for determining an order to display the user interface features based at least in part on the physiological data and the received data associated with previous user engagement, wherein determining the content layout is based at least in part on determining the order.

In some examples, the content component 635 may be configured as or otherwise support a means for determining a ranking of the user interface features based at least in part on the physiological data and the received data associated with previous user engagement, wherein determining the order is based at least in part on determining the ranking.

In some examples, the content component 635 may be configured as or otherwise support a means for determining a size of the user interface features based at least in part on the physiological data and the received data associated with previous user engagement, wherein determining the content layout is based at least in part on determining the size.

In some examples, the data acquisition component 625 may be configured as or otherwise support a means for determining that the physiological data from the wearable device associated with the user satisfies one or more thresholds. In some examples, the user interface component 640 may be configured as or otherwise support a means for causing the graphical user interface of the user device to display an alert based at least in part on determining that the physiological data satisfies the one or more thresholds, wherein the determined content layout comprises the alert.

In some examples, the data acquisition component 625 may be configured as or otherwise support a means for determining that the physiological data from the wearable device associated with the user satisfies one or more thresholds. In some examples, the user interface component 640 may be configured as or otherwise support a means for causing the graphical user interface of the user device to display a message based at least in part on determining that the physiological data satisfies the one or more thresholds, wherein the determined content layout comprises the message.

In some examples, the content component 635 may be configured as or otherwise support a means for determining media content associated with the user interface features within the application based at least in part on the physiological data and the received data associated with previous user engagement, wherein determining the content layout is based at least in part on determining the media content.

In some examples, the media content comprises a recommended video associated with the physiological data, a recommended audio associated with the physiological data, a request to input symptoms associated with the physiological data, a pattern detected from the physiological data, a confirmation of the physiological data, a suggested tag associated with the physiological data, or a combination thereof.

In some examples, the content component 635 may be configured as or otherwise support a means for determining metadata associated with the received data associated with previous user engagement, wherein the metadata comprises a quantity of times the application is accessed, a quantity of user interface features accessed, an indication of which user interface features were accessed, a duration of time that the user accesses the application, a duration of time that the user accesses a user interface feature of the user interface features, a time of day that the user accesses the application, wherein determining the content layout is based at least in part on determining the metadata.

In some examples, the user engagement component 630 may be configured as or otherwise support a means for receiving, via the user device associated with the user, indications of user engagement with the user interface features of the determined content layout based at least in part on causing the graphical user interface of the user device to display the determined content layout. In some examples, the content component 635 may be configured as or otherwise support a means for determining an updated content layout of the user interface features within the application based at least in part on a predictive model output configured to increase the future user engagement with the user interface features and the received indications of user engagement with the user interface features of the determined content layout.

In some examples, to support determining the content layout based at least in part on the output of the predictive model, the data acquisition component 625 may be configured as or otherwise support a means for inputting the physiological data into a machine learning classifier.

In some examples, the wearable device comprises a wearable ring device.

In some examples, the wearable device collects the physiological data from the user based on arterial blood flow.

Figure 7:
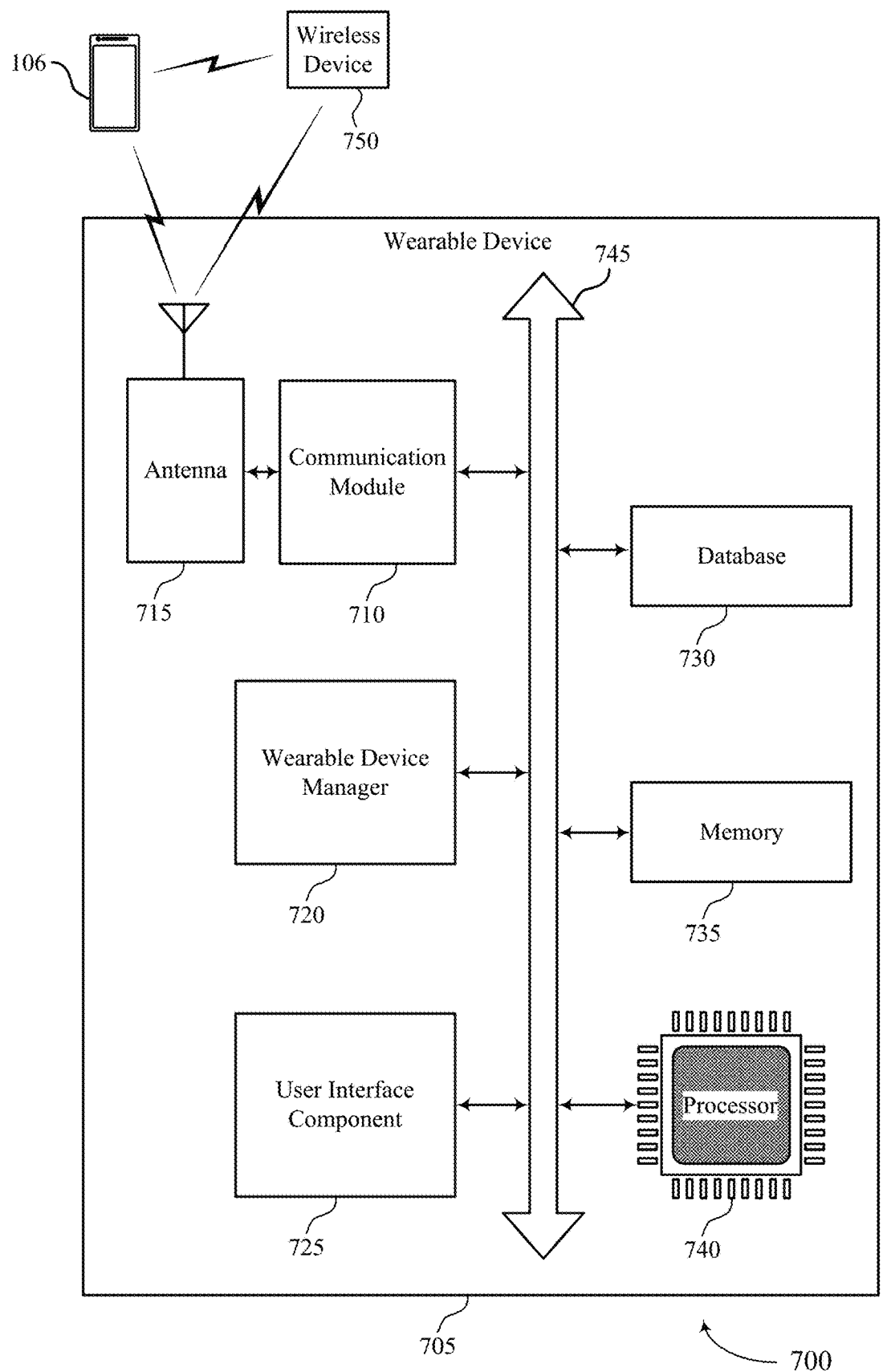
FIG. 7 shows a diagram of a system including a device that supports techniques for application personalization in accordance with aspects of the present disclosure.

FIG. 7 shows a diagram of a system 700 including a device 705 that supports techniques for application personalization in accordance with aspects of the present disclosure. The device 705 may be an example of or include the components of a device 505 as described herein. The device 705 may include components for bi-directional voice and data communications including components for transmitting and receiving communications, such as a wearable device manager 720, a communication module 710, an antenna 715, a user interface component 725, a database 730, a memory 735, a processor 740, and a wireless device 750. These components may be in electronic communication or otherwise coupled (e.g., operatively, communicatively, functionally, electronically, electrically) via one or more buses (e.g., a bus 745).

The communication module 710 may manage input and output signals for the device 705 via the antenna 715. The communication module 710 may include an example of the communication module 220-b of the user device 106 shown and described in FIG. 2. In this regard, the communication module 710 may manage communications with the ring 104 and the server 110, as illustrated in FIG. 2. The communication module 710 may also manage peripherals not integrated into the device 705. In some cases, the communication module 710 may represent a physical connection or port to an external peripheral. In some cases, the communication module 710 may utilize an operating system such as iOS®, ANDROID®, MS-DOS®, MS-WINDOWS®, OS/2®, UNIX®, LINUX®, or another known operating system. In other cases, the communication module 710 may represent or interact with a wearable device (e.g., ring 104), modem, a keyboard, a mouse, a touchscreen, or a similar device. In some cases, the communication module 710 may be implemented as part of the processor 740. In some examples, a user may interact with the device 705 via the communication module 710, user interface component 725, or via hardware components controlled by the communication module 710.

In some cases, the device 705 may include a single antenna 715. However, in some other cases, the device 705 may have more than one antenna 715, that may be capable of concurrently transmitting or receiving multiple wireless transmissions. The communication module 710 may communicate bi-directionally, via the one or more antennas 715, wired, or wireless links as described herein. For example, the communication module 710 may represent a wireless transceiver and may communicate bi-directionally with another wireless transceiver. The communication module 710 may also include a modem to modulate the packets, to provide the modulated packets to one or more antennas 715 for transmission, and to demodulate packets received from the one or more antennas 715.

The user interface component 725 may manage data storage and processing in a database 730. In some cases, a user may interact with the user interface component 725. In other cases, the user interface component 725 may operate automatically without user interaction. The database 730 may be an example of a single database, a distributed database, multiple distributed databases, a data store, a data lake, or an emergency backup database.

The memory 735 may include RAM and ROM. The memory 735 may store computer-readable, computer-executable software including instructions that, when executed, cause the processor 740 to perform various functions described herein. In some cases, the memory 7Error! Reference source not found.35 may contain, among other things, a BIOS that may control basic hardware or software operation such as the interaction with peripheral components or devices.

The processor 740 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 740 may be configured to operate a memory array using a memory controller. In other cases, a memory controller may be integrated into the processor 740. The processor 740 may be configured to execute computer-readable instructions stored in a memory 735 to perform various functions (e.g., functions or tasks supporting a method and system for sleep staging algorithms).

For example, the wearable device manager 720 may be configured as or otherwise support a means for receiving physiological data from a wearable device associated with a user. The wearable device manager 720 may be configured as or otherwise support a means for receiving, via a user device associated with the user, data associated with previous user engagement by the user with user interface features of an application associated with the wearable device, wherein the application associated with the wearable device is configured to process and display the physiological data received from the wearable device to the user via the user device. The wearable device manager 720 may be configured as or otherwise support a means for determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input. The wearable device manager 720 may be configured as or otherwise support a means for causing a graphical user interface of the user device to display the determined content layout of the user interface features. Although the wearable device manager 720 is displayed as a component of wearable device, as described herein, it is to be understood that components or functionality of wearable device manager 720 may be implemented by a user device 106, a wireless device 750, a server, or some combination of these devices.

By including or configuring the wearable device manager 720 in accordance with examples as described herein, the device 705 may support techniques for improved application personalization. In particular, techniques described herein may enable improved communication reliability, reduced latency, improved user experience related to reduced processing, reduced power consumption, more efficient utilization of communication resources, improved coordination between devices, longer battery life, and improved utilization of processing capability.

Figure 8:
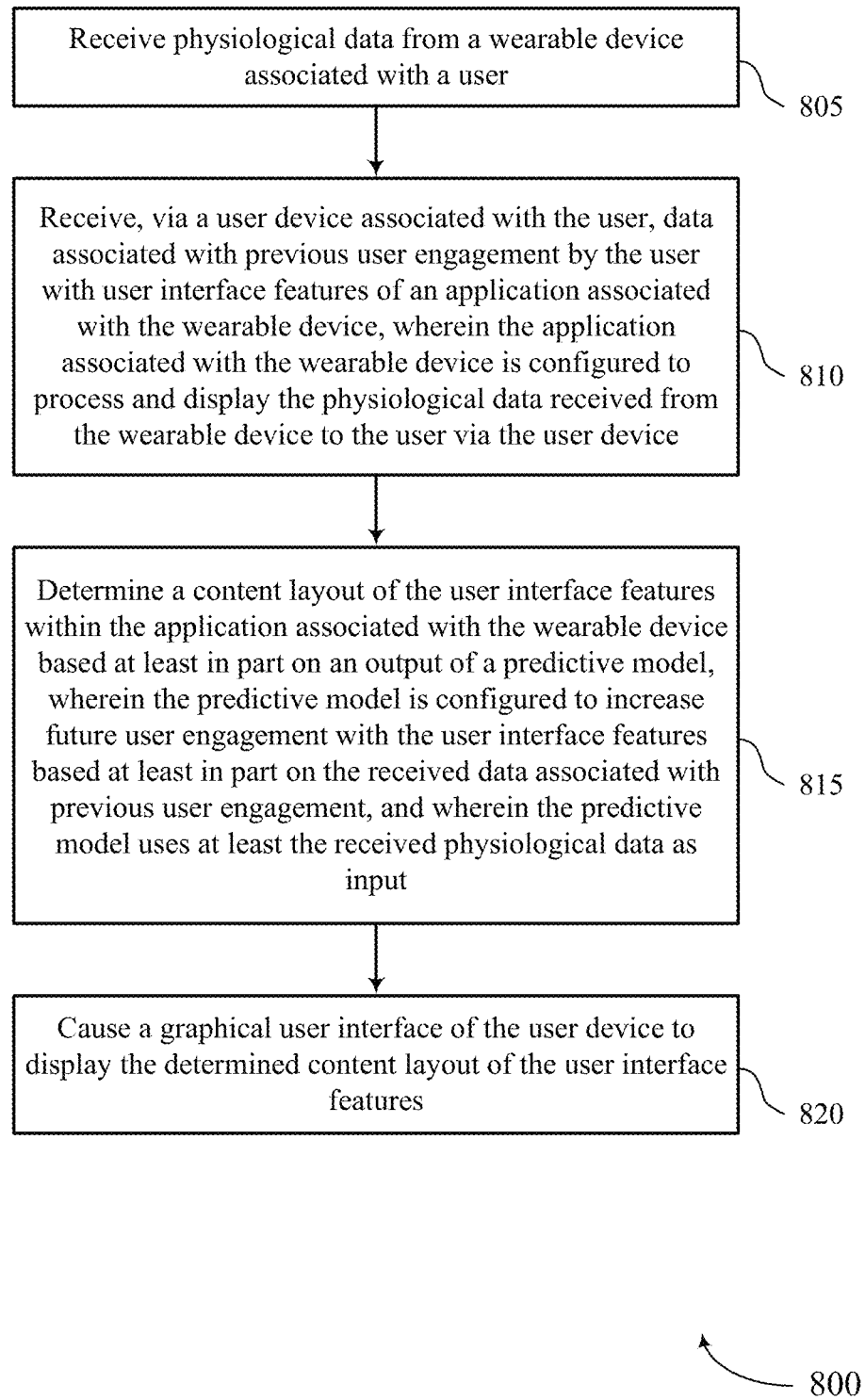
FIGS. 8 through 10 show flowcharts illustrating methods that support techniques for application personalization in accordance with aspects of the present disclosure.

FIG. 8 shows a flowchart illustrating a method 800 that supports techniques for application personalization in accordance with aspects of the present disclosure. The operations of the method 800 may be implemented by a wearable device, a user device, a server, or a combination of components from one or more of these devices as described herein. For example, the operations of the method 800 may be performed by a wearable device, user device, or server as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 805, the method may include receiving physiological data from a wearable device associated with a user. The operations of 805 may be performed in accordance with examples as disclosed herein. In some examples, aspects of the operations of 805 may be performed by a data acquisition component 625 as described with reference to FIG. 6.

At 810, the method may include receiving, via a user device associated with the user, data associated with previous user engagement by the user with user interface features of an application associated with the wearable device, wherein the application associated with the wearable device is configured to process and display the physiological data received from the wearable device to the user via the user device. The operations of 810 may be performed in accordance with examples as disclosed herein. In some examples, aspects of the operations of 810 may be performed by a user engagement component 630 as described with reference to FIG. 6.

At 815, the method may include determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input. The operations of 815 may be performed in accordance with examples as disclosed herein. In some examples, aspects of the operations of 815 may be performed by a content component 635 as described with reference to FIG. 6.

At 820, the method may include causing a graphical user interface of the user device to display the determined content layout of the user interface features. The operations of 820 may be performed in accordance with examples as disclosed herein. In some examples, aspects of the operations of 820 may be performed by a user interface component 640 as described with reference to FIG. 6.

Figure 9:
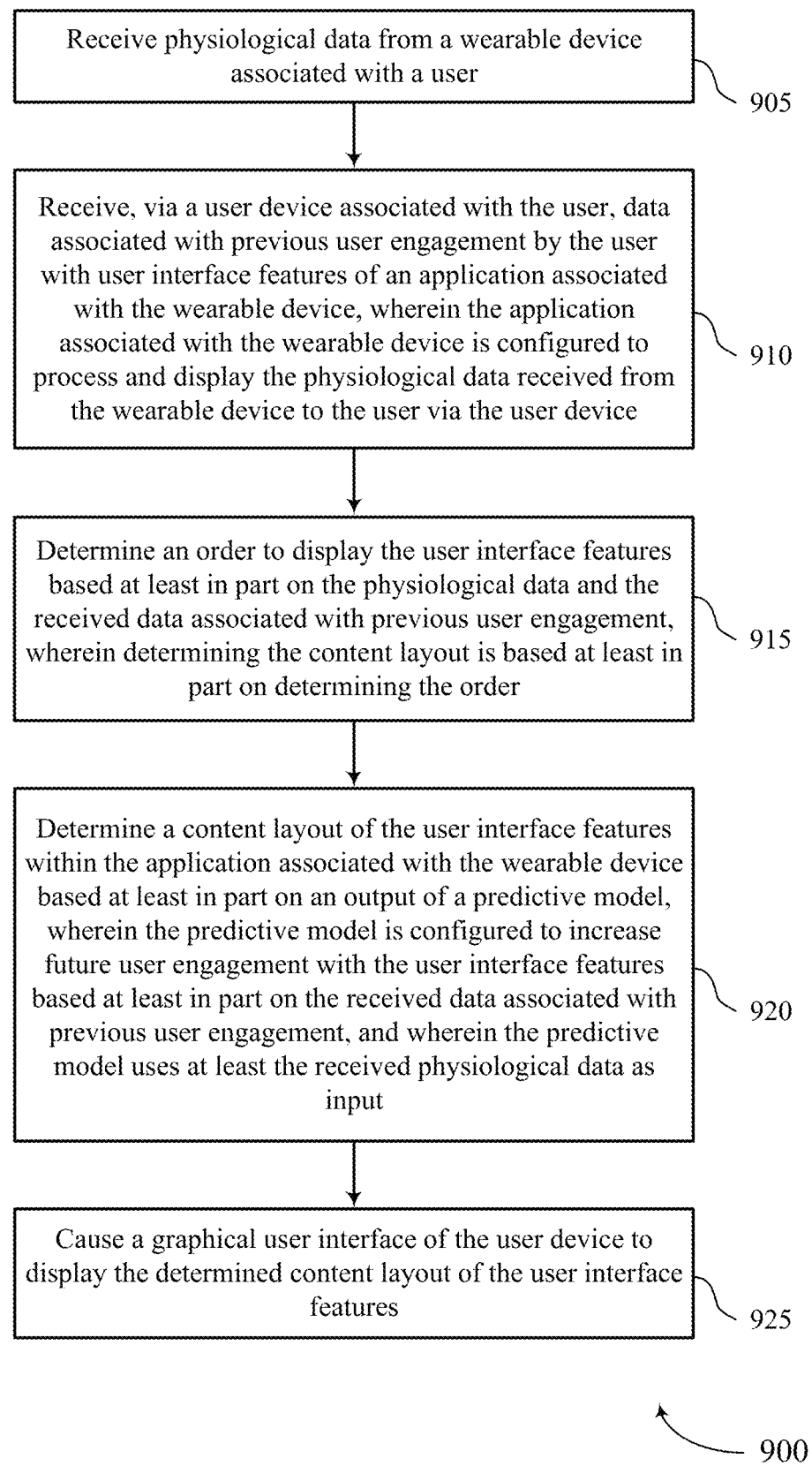

FIG. 9 shows a flowchart illustrating a method 900 that supports techniques for application personalization in accordance with aspects of the present disclosure. The operations of the method 900 may be implemented by a wearable device, a user device, a server, or a combination of components from one or more of these devices as described herein. For example, the operations of the method 900 may be performed by a wearable device, a user device, a server, or a combination of components from one or more of these devices as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 905, the method may include receiving physiological data from a wearable device associated with a user. The operations of 905 may be performed in accordance with examples as disclosed herein. In some examples, aspects of the operations of 905 may be performed by a data acquisition component 625 as described with reference to FIG. 6.

At 910, the method may include receiving, via a user device associated with the user, data associated with previous user engagement by the user with user interface features of an application associated with the wearable device, wherein the application associated with the wearable device is configured to process and display the physiological data received from the wearable device to the user via the user device. The operations of 910 may be performed in accordance with examples as disclosed herein. In some examples, aspects of the operations of 910 may be performed by a user engagement component 630 as described with reference to FIG. 6.

At 915, the method may include determining an order to display the user interface features based at least in part on the physiological data and the received data associated with previous user engagement, wherein determining the content layout is based at least in part on determining the order. The operations of 915 may be performed in accordance with examples as disclosed herein. In some examples, aspects of the operations of 915 may be performed by a content component 635 as described with reference to FIG. 6.

At 920, the method may include determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input. The operations of 920 may be performed in accordance with examples as disclosed herein. In some examples, aspects of the operations of 920 may be performed by a content component 635 as described with reference to FIG. 6.

At 925, the method may include causing a graphical user interface of the user device to display the determined content layout of the user interface features. The operations of 925 may be performed in accordance with examples as disclosed herein. In some examples, aspects of the operations of 925 may be performed by a user interface component 640 as described with reference to FIG. 6.

Figure 10:
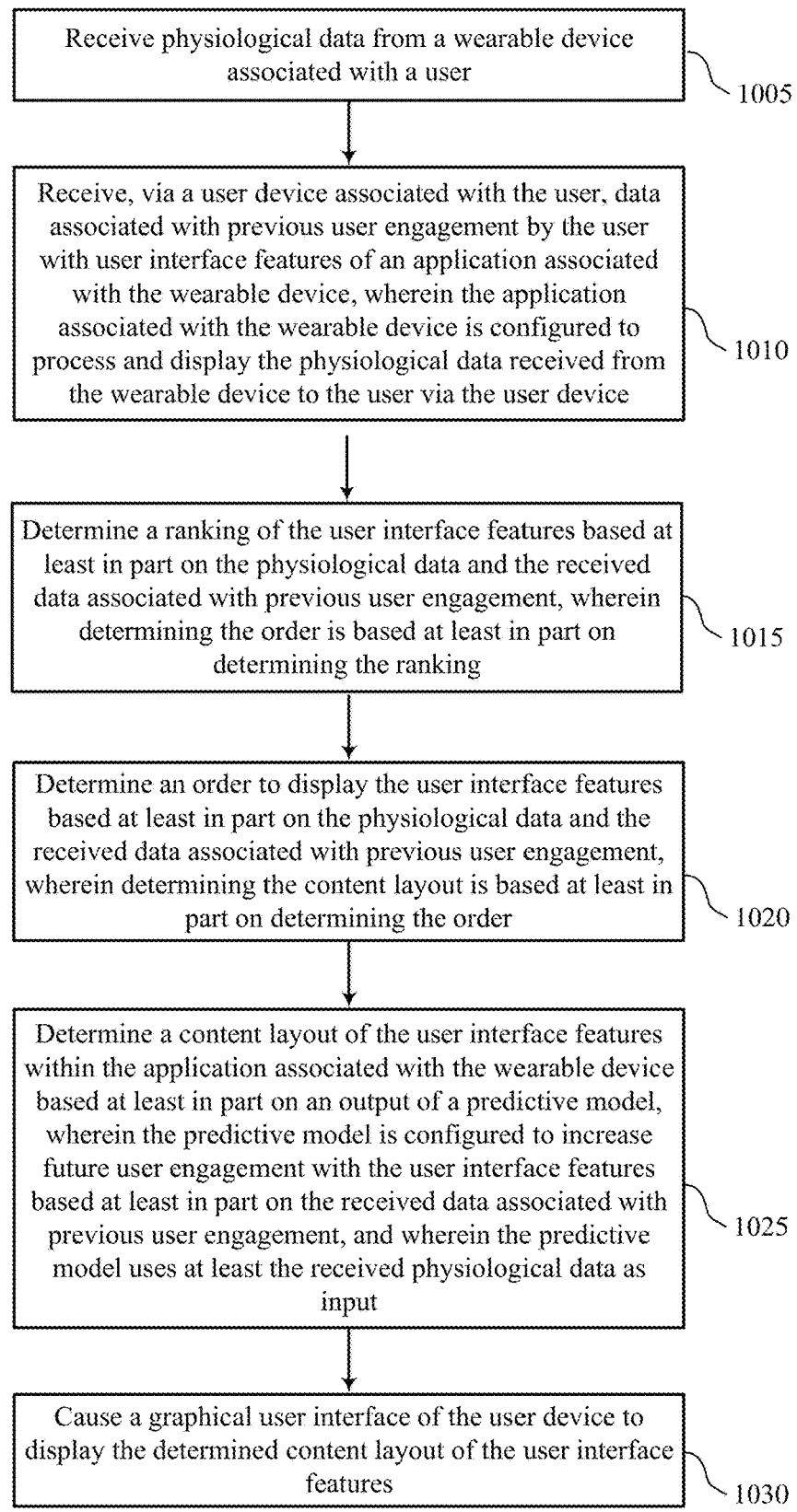

FIG. 10 shows a flowchart illustrating a method 1000 that supports techniques for application personalization in accordance with aspects of the present disclosure. The operations of the method 1000 may be implemented by a wearable device, a user device, a server, or a combination of components from one or more of these devices as described herein. For example, the operations of the method 1000 may be performed by a wearable device, a user device, a server, or a combination of components from one or more of these devices as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 1005, the method may include receiving physiological data from a wearable device associated with a user. The operations of 1005 may be performed in accordance with examples as disclosed herein. In some examples, aspects of the operations of 1005 may be performed by a data acquisition component 625 as described with reference to FIG. 6.

At 1010, the method may include receiving, via a user device associated with the user, data associated with previous user engagement by the user with user interface features of an application associated with the wearable device, wherein the application associated with the wearable device is configured to process and display the physiological data received from the wearable device to the user via the user device. The operations of 1010 may be performed in accordance with examples as disclosed herein. In some examples, aspects of the operations of 1010 may be performed by a user engagement component 630 as described with reference to FIG. 6.

At 1015, the method may include determining a ranking of the user interface features based at least in part on the physiological data and the received data associated with previous user engagement, wherein determining the order is based at least in part on determining the ranking. The operations of 1015 may be performed in accordance with examples as disclosed herein. In some examples, aspects of the operations of 1015 may be performed by a content component 635 as described with reference to FIG. 6.

At 1020, the method may include determining an order to display the user interface features based at least in part on the physiological data and the received data associated with previous user engagement, wherein determining the content layout is based at least in part on determining the order. The operations of 1020 may be performed in accordance with examples as disclosed herein. In some examples, aspects of the operations of 1020 may be performed by a content component 635 as described with reference to FIG. 6.

At 1025, the method may include determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input. The operations of 1025 may be performed in accordance with examples as disclosed herein. In some examples, aspects of the operations of 1025 may be performed by a content component 635 as described with reference to FIG. 6.

At 1030, the method may include causing a graphical user interface of the user device to display the determined content layout of the user interface features. The operations of 1030 may be performed in accordance with examples as disclosed herein. In some examples, aspects of the operations of 1030 may be performed by a user interface component 640 as described with reference to FIG. 6.

A method is described. The method may include receiving physiological data from a wearable device associated with a user, receiving, via a user device associated with the user, data associated with previous user engagement by the user with user interface features of an application associated with the wearable device, wherein the application associated with the wearable device is configured to process and display the physiological data received from the wearable device to the user via the user device, determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input, and causing a graphical user interface of the user device to display the determined content layout of the user interface features.

An apparatus is described. The apparatus may include a processor, memory coupled with the processor, and instructions stored in the memory. The instructions may be executable by the processor to cause the apparatus to receive physiological data from a wearable device associated with a user, receive, via a user device associated with the user, data associated with previous user engagement by the user with user interface features of an application associated with the wearable device, wherein the application associated with the wearable device is configured to process and display the physiological data received from the wearable device to the user via the user device, determine a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input, and cause a graphical user interface of the user device to display the determined content layout of the user interface features.

Another apparatus is described. The apparatus may include means for receiving physiological data from a wearable device associated with a user, means for receiving, via a user device associated with the user, data associated with previous user engagement by the user with user interface features of an application associated with the wearable device, wherein the application associated with the wearable device is configured to process and display the physiological data received from the wearable device to the user via the user device, means for determining a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input, and means for causing a graphical user interface of the user device to display the determined content layout of the user interface features.

A non-transitory computer-readable medium storing code is described. The code may include instructions executable by a processor to receive physiological data from a wearable device associated with a user, receive, via a user device associated with the user, data associated with previous user engagement by the user with user interface features of an application associated with the wearable device, wherein the application associated with the wearable device is configured to process and display the physiological data received from the wearable device to the user via the user device, determine a content layout of the user interface features within the application associated with the wearable device based at least in part on an output of a predictive model, wherein the predictive model is configured to increase future user engagement with the user interface features based at least in part on the received data associated with previous user engagement, and wherein the predictive model uses at least the received physiological data as input, and cause a graphical user interface of the user device to display the determined content layout of the user interface features.

Some examples of the method, apparatuses, and non-transitory computer-readable medium described herein may further include operations, features, means, or instructions for determining an order to display the user interface features based at least in part on the physiological data and the received data associated with previous user engagement, wherein determining the content layout may be based at least in part on determining the order.

Some examples of the method, apparatuses, and non-transitory computer-readable medium described herein may further include operations, features, means, or instructions for determining a ranking of the user interface features based at least in part on the physiological data and the received data associated with previous user engagement, wherein determining the order may be based at least in part on determining the ranking.

Some examples of the method, apparatuses, and non-transitory computer-readable medium described herein may further include operations, features, means, or instructions for determining a size of the user interface features based at least in part on the physiological data and the received data associated with previous user engagement, wherein determining the content layout may be based at least in part on determining the size.

Some examples of the method, apparatuses, and non-transitory computer-readable medium described herein may further include operations, features, means, or instructions for determining that the physiological data from the wearable device associated with the user satisfies one or more thresholds and causing the graphical user interface of the user device to display an alert based at least in part on determining that the physiological data satisfies the one or more thresholds, wherein the determined content layout comprises the alert.

Some examples of the method, apparatuses, and non-transitory computer-readable medium described herein may further include operations, features, means, or instructions for determining that the physiological data from the wearable device associated with the user satisfies one or more thresholds and causing the graphical user interface of the user device to display a message based at least in part on determining that the physiological data satisfies the one or more thresholds, wherein the determined content layout comprises the message.

Some examples of the method, apparatuses, and non-transitory computer-readable medium described herein may further include operations, features, means, or instructions for determining media content associated with the user interface features within the application based at least in part on the physiological data and the received data associated with previous user engagement, wherein determining the content layout may be based at least in part on determining the media content.

In some examples of the method, apparatuses, and non-transitory computer-readable medium described herein, the media content comprises a recommended video associated with the physiological data, a recommended audio associated with the physiological data, a request to input symptoms associated with the physiological data, a pattern detected from the physiological data, a confirmation of the physiological data, a suggested tag associated with the physiological data, or a combination thereof.

Some examples of the method, apparatuses, and non-transitory computer-readable medium described herein may further include operations, features, means, or instructions for determining metadata associated with the received data associated with previous user engagement, wherein the metadata comprises a quantity of times the application may be accessed, a quantity of user interface features accessed, an indication of which user interface features were accessed, a duration of time that the user accesses the application, a duration of time that the user accesses a user interface feature of the user interface features, a time of day that the user accesses the application, wherein determining the content layout may be based at least in part on determining the metadata.

Some examples of the method, apparatuses, and non-transitory computer-readable medium described herein may further include operations, features, means, or instructions for receiving, via the user device associated with the user, indications of user engagement with the user interface features of the determined content layout based at least in part on causing the graphical user interface of the user device to display the determined content layout and determining an updated content layout of the user interface features within the application based at least in part on a predictive model output configured to increase the future user engagement with the user interface features and the received indications of user engagement with the user interface features of the determined content layout.

In some examples of the method, apparatuses, and non-transitory computer-readable medium described herein, determining the content layout based at least in part on the output of the predictive model may include operations, features, means, or instructions for inputting the physiological data into a machine learning classifier.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method, comprising:
receiving physiological data from a wearable device associated with a user;
receiving, via a user device associated with the user, data associated with previous user engagement by the user with user interface features of an application associated with the wearable device, wherein the application associated with the wearable device is configured to process and display the physiological data received from the wearable device to the user via the user device;
inputting, into a predictive model configured to increase future user engagement with the user interface features, the physiological data received from the wearable device and the data associated with previous user engagement by the user with the user interface features;
determining a content layout of the user interface features within the application associated with the wearable device based at least in part on an output of the predictive model; and
causing a graphical user interface of the user device to display the content layout of the user interface features.

2. The method of claim 1, further comprising:
determining an order to display the user interface features based at least in part on the physiological data and the data associated with previous user engagement, wherein determining the content layout is based at least in part on determining the order.

3. The method of claim 2, further comprising:
determining a ranking of the user interface features based at least in part on the physiological data and the data associated with previous user engagement, wherein determining the order is based at least in part on determining the ranking.

4. The method of claim 1, further comprising:
determining a size of the user interface features based at least in part on the physiological data and the data associated with previous user engagement, wherein determining the content layout is based at least in part on determining the size.

5. The method of claim 1, further comprising:
determining that the physiological data from the wearable device associated with the user satisfies one or more thresholds; and
causing the graphical user interface of the user device to display an alert based at least in part on determining that the physiological data satisfies the one or more thresholds, wherein the content layout comprises the alert.

6. The method of claim 1, further comprising:
determining that the physiological data from the wearable device associated with the user satisfies one or more thresholds; and
causing the graphical user interface of the user device to display a message based at least in part on determining that the physiological data satisfies the one or more thresholds, wherein the content layout comprises the message.

7. The method of claim 1, further comprising:
determining media content associated with the user interface features within the application based at least in part on the physiological data and the data associated with previous user engagement, wherein determining the content layout is based at least in part on determining the media content.

8. The method of claim 7, wherein the media content comprises a recommended video associated with the physiological data, a recommended audio associated with the physiological data, a request to input symptoms associated with the physiological data, a pattern detected from the physiological data, a confirmation of the physiological data, a suggested tag associated with the physiological data, or a combination thereof.

9. The method of claim 1, further comprising:
determining metadata associated with the data associated with previous user engagement, wherein the metadata comprises a quantity of times the application is accessed, a quantity of user interface features accessed, an indication of which user interface features were accessed, a duration of time that the user accesses the application, a duration of time that the user accesses a user interface feature of the user interface features, a time of day that the user accesses the application, wherein determining the content layout is based at least in part on determining the metadata.

10. The method of claim 1, further comprising:
receiving, via the user device associated with the user, indications of user engagement with the user interface features of the content layout based at least in part on causing the graphical user interface of the user device to display the content layout; and
determining an updated content layout of the user interface features within the application based at least in part on a predictive model output configured to increase the future user engagement with the user interface features and the indications of user engagement with the user interface features of the content layout.

11. The method of claim 1, wherein determining the content layout based at least in part on the output of the predictive model further comprises:
inputting the physiological data into a machine learning classifier.

12. The method of claim 1, wherein the wearable device comprises a wearable ring device.

13. The method of claim 1, wherein the wearable device collects the physiological data from the user based on arterial blood flow.

14. An apparatus, comprising:
a processor;
memory coupled with the processor; and
instructions stored in the memory and executable by the processor to cause the apparatus to:
receive physiological data from a wearable device associated with a user;
receive, via a user device associated with the user, data associated with previous user engagement by the user with user interface features of an application associated with the wearable device, wherein the application associated with the wearable device is configured to process and display the physiological data received from the wearable device to the user via the user device;
input, into a predictive model configured to increase future user engagement with the user interface features, the physiological data received from the wearable device and the data associated with previous user engagement by the user with the user interface features;
determine a content layout of the user interface features within the application associated with the wearable device based at least in part on an output of the predictive model; and
cause a graphical user interface of the user device to display the content layout of the user interface features.

15. The apparatus of claim 14, wherein the instructions are further executable by the processor to cause the apparatus to:
determine an order to display the user interface features based at least in part on the physiological data and the data associated with previous user engagement, wherein determining the content layout is based at least in part on determining the order.

16. The apparatus of claim 15, wherein the instructions are further executable by the processor to cause the apparatus to:
determine a ranking of the user interface features based at least in part on the physiological data and the data associated with previous user engagement, wherein determining the order is based at least in part on determining the ranking.

17. The apparatus of claim 14, wherein the instructions are further executable by the processor to cause the apparatus to:
determine a size of the user interface features based at least in part on the physiological data and the data associated with previous user engagement, wherein determining the content layout is based at least in part on determining the size.

18. A non-transitory computer-readable medium storing code, the code comprising instructions executable by a processor to:
receive physiological data from a wearable device associated with a user;
receive, via a user device associated with the user, data associated with previous user engagement by the user with user interface features of an application associated with the wearable device, wherein the application associated with the wearable device is configured to process and display the physiological data received from the wearable device to the user via the user device;
input, into a predictive model configured to increase future user engagement with the user interface features, the physiological data received from the wearable device and the data associated with previous user engagement by the user with the user interface features;
determine a content layout of the user interface features within the application associated with the wearable device based at least in part on an output of the predictive model; and
cause a graphical user interface of the user device to display the content layout of the user interface features.

19. The non-transitory computer-readable medium of claim 18, wherein the instructions are further executable by the processor to:

determine an order to display the user interface features based at least in part on the physiological data and the data associated with previous user engagement, wherein determining the content layout is based at least in part on determining the order.

20. The non-transitory computer-readable medium of claim 19, wherein the instructions are further executable by the processor to:

determine a ranking of the user interface features based at least in part on the physiological data and the data associated with previous user engagement, wherein determining the order is based at least in part on determining the ranking.

\* \* \* \* \*